United States Patent [19]
Gwinner

[11] Patent Number: 4,848,719
[45] Date of Patent: Jul. 18, 1989

[54] MOLD FOR EMBEDDING HISTOLOGICAL PREPARATIONS

[75] Inventor: Lutz Gwinner, Mainz, Fed. Rep. of Germany

[73] Assignee: Kulzer & Co., GmbH, Wehrheim, Fed. Rep. of Germany

[21] Appl. No.: 162,164

[22] Filed: Feb. 29, 1988

[30] Foreign Application Priority Data

Mar. 7, 1987 [DE] Fed. Rep. of Germany ....... 3707400

[51] Int. Cl.⁴ ............................................. B29C 33/68
[52] U.S. Cl. .................. 249/114.1; 249/115; 249/117; 249/127
[58] Field of Search .................. 249/114 R, 127, 117, 249/114.1, 112; 99/DIG. 15; 264/338, 22; 425/410

[56] References Cited

U.S. PATENT DOCUMENTS

| 14,327 | 9/1883 | Mazzetti | 249/117 |
|---|---|---|---|
| 382,678 | 5/1888 | Ball | 249/119 |
| 1,568,696 | 1/1926 | Smythe | 249/117 |
| 1,701,619 | 2/1929 | Kendall | 249/127 |
| 2,478,165 | 8/1949 | Collins | 249/114 |
| 2,540,731 | 2/1951 | Hildebrandt | 249/117 |
| 2,583,887 | 1/1952 | Schneeweiss | 99/DIG. 15 |
| 3,214,128 | 10/1965 | Beck et al. | 249/127 |
| 3,217,617 | 11/1965 | Wiswell | 249/114 |
| 3,615,071 | 10/1971 | Harper | 249/114 |
| 3,759,478 | 9/1973 | Schmitt et al. | 249/117 |
| 3,883,109 | 5/1975 | Hahne | 249/127 |
| 4,458,875 | 7/1984 | Bolton | 249/114 R |
| 4,492,664 | 1/1985 | Bruno | 264/338 |
| 4,546,900 | 10/1985 | Lackey | 249/127 |
| 4,598,050 | 7/1986 | Brown | 435/298 |
| 4,647,000 | 3/1987 | Osada | 249/127 |

FOREIGN PATENT DOCUMENTS 1923709 11/1970 Fed. Rep. of Germany ...... 249/117
0403805 11/1909 France ......................... 99/DIG. 15

Primary Examiner—Willard Hoag
Attorney, Agent, or Firm—Frishauf, Holtz, Goodman & Woodward

[57] ABSTRACT

A mold for embedding histological specimens made of transparent plastic of the kind that is hardenable by irradiation, usually with light, consists of at least one flat-bottomed oval basin depressed with respect to a surrounding surface which, in turn, is externally bounded by a peripheral channel. The containing walls of the basin are outwardly inclined from the vertical. A separating layer covers the entire upper surfaces of the mold, including those of the peripheral channel, and consists of a synthetic resin, such as polyethylene, which does not bond with the resin of the embedding material and can be applied to the sheet of acrylic resin or polyvinyl chloride before the latter is pressed into the shape of the mold. The specimen embedded in the hardened embedding resin can be easily expelled from the mold even if the mold is made from another resin to which the separation layer might bond.

12 Claims, 3 Drawing Sheets

MOLD FOR EMBEDDING HISTOLOGICAL PREPARATIONS

This invention concerns an open-top mold for use for embedding histological preparations in a mass of synthetic resin. The mold is a flat-bottomed shell having an upwardly drawn rim and is made of transparent material.

Microscopic investigations of both hard and soft body tissues are frequently carried out in the study and investigation of histology which is the science of living tissue. "Histology" also means an analytic technical procedure for carrying out morphological and histochemical investigations on samples of hard or soft tissues. Since the microscopic investigations must be carried out on thin slices of a thickness of about 1 $\mu$m, the tissues to be investigated must first be cast in an embedding material in order then to produce a thin slice or polished section from the cast perforation. The synthetic resins used for embedding histological preparations are principally those that are hardened by irradiation, usually with ultra-violet light.

The embedding mass is filled into shell or dish-shaped molds of glass or synthetic resin, which under present practice are knocked or broken to pieces after hardening of the embedding mass, since otherwise the embedding mass could be loosened from the mold only with great difficulty. Furthermore, with such molds the edges are wetted with the embedding material during pouring into the mold or by overflow of the material, thus making it still more difficult to loosen the hardened mass from the mold. Shells or dishes of similar shape are also used for growing cultures of microorganisms. A culture dish for such purposes is known from U.S. Pat. No. 4,598,050. The dish there described can be closed above with a cover. A number of inserts are provided in the dish, among other things for introducing a nutrient medium.

SUMMARY OF THE INVENTION

It is an object of the present invention to provide a basin mold for embedding histological preparations in resin masses with the advantage of uniform loosening of the hardened embedding mass in the region of the bottom and the side walls and if necessary at the rim of the mold.

Briefly, at least in the region of the basin bottom and in the region of the rim surface extending from the outer edge of the bottom, the mold has a separation layer or release layer on its inner surface which is provided by a film or foil. As the result of the film or foil inserted between the embedding mass and the mold, it is possible to loosen the hardened embedding material easily from the mold. The film or foil, after the hardening of the contents, either does not bond at all with the surfaces in contact with it, or else bonds only to the hardened embedding mass. It has been observed, however, that the foil, especially when a polyethylene film is utilized as the inserted foil, does not even bond with the embedding mass. This might result from the different expansion coefficients of the mold, the foil and the embedding material. The foil is preferably pressed onto the plate or flat sheet material from which the mold is, for example, deep-drawn. The thickness of the foil should be between 1 and 50 $\mu$m, preferably between 5 and 10 $\mu$m. A mold of acrylic resin or of polyvinyl chloride is particularly suitable for the mold of the invention, because such molds are distinguished by their good transparency on the one hand and resistance to deformation on the other hand, while still remaining sufficiently flexible in order to permit the hardened embedding mass to be pushed out of the mold.

Particularly with reference to providing good stability and nevertheless sufficient elasticity in the region of the bottom, the bottom of the mold should have a round or oval outer contour. For the same reason, the wall surface of the mold should be inclined outwardly, so that the basin which accepts the embedding mass should widen towards its rim. An angle of inclination of the rim walls to the direction perpendicular to the bottom of the mold in the range from 5° to 30° has been found satisfactory.

At the rim edge of the rim walls there can be joined a rim flange or rim strip turned outwardly over towards the bottom, by which the rim of the mold is additionally reinforced. This rim strip also should be covered by the foil or film which coats the basin bottom and the rim wall surfaces.

In a preferred embodiment, a peripheral channel is joined to to a rim flange of the mold which on the one hand can fulfill the function of the already mentioned turned over rim and, on the other hand, serves to catch embedding material slopping out of the dish or basin region. In this way there is assured a resetting of a filling level for a content quantity of the embedding mass filling which is identical from mold to mold. A particular advantage of such a channel lies in the fact that material which overflows into the channel can be broken off in a simple way, since the embedding material does not bond with the channel, which is coated with the release film or foil like the rest of the upper side of the mold.

In the case in which the outer channel wall extends in height above the inner channel wall, there is the advantage of easier removal or insertion of the mold from or into a carrier or directly from or into an irradiation apparatus.

The thickness of the bottom of the mold is preferably in the region from 0.1 to 1 mm. The rim wall surface should have a height of between 5 and 15 mm, dependent upon the particular preparations which are to be embedded.

BRIEF DESCRIPTION OF THE DRAWINGS

The invention is further described by way of illustrative example with reference to the annexed drawings, in which.

DESCRIPTION OF THE ILLUSTRATED EMBODIMENTS

Figure 5:
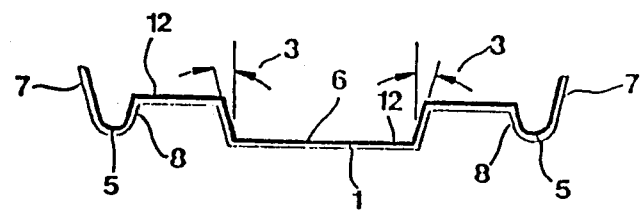
FIG. 5 is a cross section of the mold of FIG. 3 along the line V—V of FIG. 3.
Figure 6:
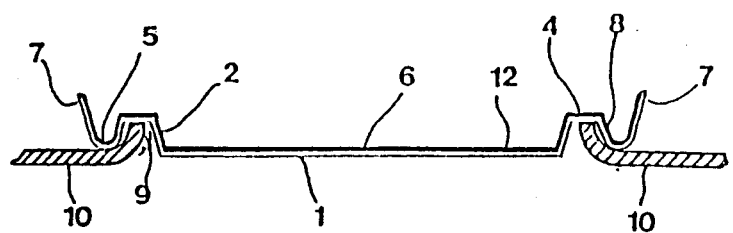
FIG. 6 is a cross section showing a mold according to the invention seated in a holder.

In the illustrated examples of molds according to the invention, the bottom portion 1 in each case has an oval contour, around which lie the outwardly inclined containing walls 2. The inclination of these walls 2 shown by the angle 3 in FIGS. 2 and 5 relative to the vertical is 25°. The horizontally disposed surface 4 is connected to the rim of these containing walls 2 and leads to a peripheral channel 5. The channel 5 serves to catch overflowing embedding material from the filling of the basin or dish-shaped region 6. In consequence, an approximately equal thickness of the hardened embedding material is obtained when identical molds are used. The outer channel wall 7 projects above the level of the inner channel wall 8; by this projecting outer channel wall 7 the mold can easily be grasped with two fingers and, moreover, it is thereby assured that no embedding material comes out of the mold so long as it is kept in more or less level position. As shown in FIG. 6, the inverted channel 9 beneath the horizontal surface 4 externally bounded by the inner wall of the peripheral channel 5 makes it possible to set the horizontal surface 4 on an upturned aperture edge of an apertured holder plate 10, so as to center the mold on the aperture of the holder 10.

Figure 1:
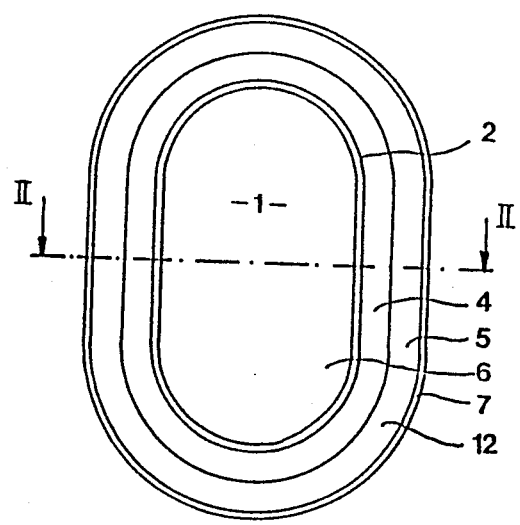
FIG. 1 is a top view of a mold according to the invention for embedding preparations.
Figure 2:
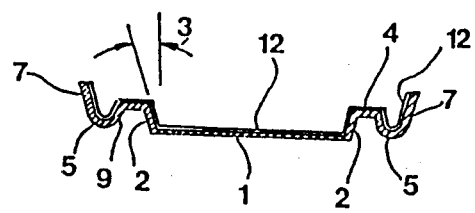
FIG. 2 is a section of the mold of FIG. 1 along the line II—II of FIG. 1.
Figure 3:
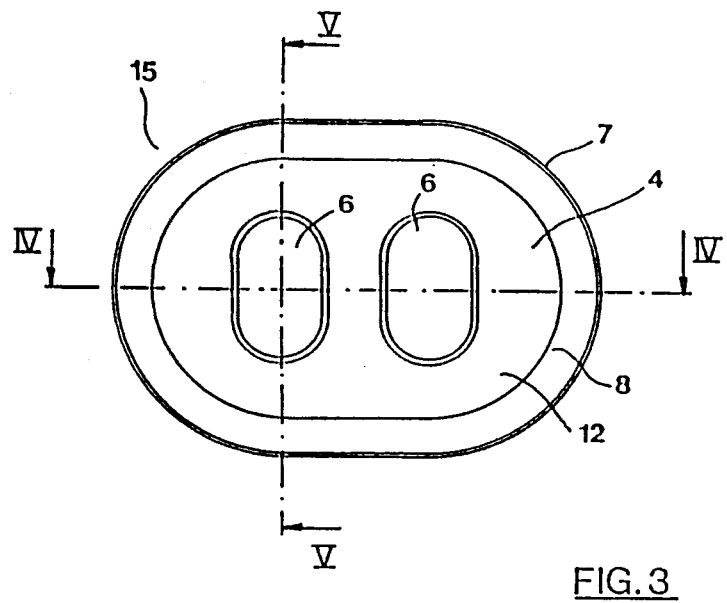
FIG. 3 is a top view of a mold for two preparations.

In contrast to the mold according to FIGS. 1 and 2, the mold according to FIGS. 3-6 has two basin-like regions 6 in each of which a preparation to be investigated can be embedded in resin.

Figure 4:
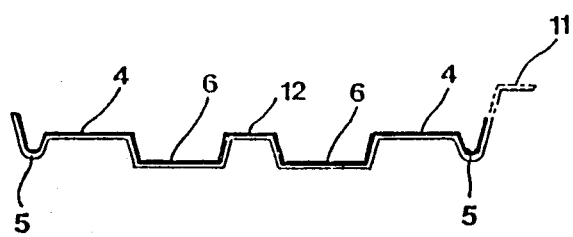
FIG. 4 is a lengthwise cross section of the mold of FIG. 3 on the line IV—IV of FIG. 3.

A further raised peripheral flat surface 11 can be provided as an extension of the outer channel wall 7, as shown in broken lines in FIG. 4. In such a case, in contrast to the mold of FIG. 6, the supplementary peripheral flat surface 11 can be used as a support surface, for example, of a cover, rather than the annular horizontal surface 4.

The peripheral channel 5 incidentally reinforces the mold against deformation and when it is provided the additional raised horizontal flange 11 may provide additional reinforcement.

In all of the embodiments shown, the separation layer 12 provided by a thin polyethylene foil or film of a thickness preferably from about 5 to 10 μm is applied on the inner side of the mold. As already mentioned, this is preferably done by applying the foil on sheet material from which the mold is to be shaped and then pressing both the plate or sheet material and the overlying foil into shape in a single operation. This separation layer or foil 12 covers not only the bottom 1 of the mold but also the containing wall surfaces 2, the peripheral channel 5 and the intervening horizontal surface 4. In this way it is assured that the embedding material hardened in the basin-shaped region is releasable after its hardening. Furthermore, the embedding material that may overflow into the peripheral channel 5 produces no bonding with the mold. After the release of the hardened embedding mass out of the mold, the embedding material that may be in the peripheral channel, which according to the filling height of the embedding mass is likely to be connected to the embedded sample by a web in the region of the horizontal surface 4 to the embedding mass in the basin region, can readily be broken off.

A further advantage of the separation layer foil 12 is that the foil surface makes available an especially smooth surface for the mold which is of importance for the basin of the mold which is filled with the embedding mass.

An example of light-hardenable embedding material is the following composition:

| % by wt. | Material |
| --- | --- |
| 20 | methyl methacrylate |
| 40 | 2-hydroxyethyl methacrylate |
| 30 | triethyleneglycol dimethacrylate |
| 9.5 | butanediol dimethacrylate |
| 0.5 | "Irgacure 651" or "Darocure 1173" (Merck) |

As already mentioned, the molds preferably are made of acrylic resin or of polyvinyl chloride, materials which are particularly well suited for the mold because of their transparency to irradiation light and their combination of resistance to deformation and a certain flexibility that facilitates expelling the hardened resin from the mold. The mold could also be made of transparent polyamide. Transparence or at least translucence is desirable because the embedding resin is commonly irradiated through the mold for hardening.

With reference to the dimensions identified in FIG. 6 for the illustrated embodiments, the thickness 13 of the mold at least in the region of its bottom 1 is preferably about 0.8 mm and the depth of the basin defined by the containing walls 2 is preferably about 8 mm, in general the thickness 13 should be between 0.05 mm and 1 mm, and the basin depth 14 between 5 and 15 mm.

Although the invention has been described with reference to particular illustrative examples, it will be understood that variations and modifications are possible within the inventive concept. Thus, for example, the separation layer may be a polypropylene film or foil instead of one of polyethylene.

I claim:

1. Mold for casting histological specimen preparations embedded in a synthetic resin hardenable by irradiation with light, comprising a basin made of material transparent to light in the wavelength range from 350 to 750 nm and containing walls surrounding and rising with an outward inclination from a bottom to a uniform height, the interior side of said basin bottom and walls having applied thereon, over the entire interior surface thereof, a separating layer formed of a foil of a polyethylene material of uniform thickness with the thickness range from 1 to 50 μm that has no tendency to stick to said irradiation-hardenable resin even when said resin is irradiation-hardened in said mold said mold having a generally flat bottom and defining a groove peripherally about said bottom, said polyethylene material conforming to inside surfaces of the mold including surfaces of the mold ncluding surfaces defining said groove.

2. Mold as defined in claim 1, wherein said thickness is within the range from 5 to 10 μm.

3. Mold as defined in claim 1, wherein said bottom is flat and said transparent material of which said basin and said mold are made is of substantially uniform thickness and consists of a synthetic resin selected from the group consisting of acrylic resins, polyvinyl chloride resins and polyamide resins.

4. Mold as defined in claim 3, wherein said bottom of said basin has a round contour.

5. Mold as defined in claim 4, wherein said round contour is circular.

6. Mold as defined in claim 4, wherein said round contour is oval.

7. Mold as defined in claim 1, wherein the angle of inclination of said walls with reference to the direction perpendicular to said bottom is in the range from 5° to 30°.

8. Mold as defined in claim 3, wherein said walls provide a rim of said basin of uniform height above said basin and said basin rim has an outwardly turned over extension.

9. Mold as defined in claim 8, wherein said outwardly turned over rim extension includes said groove.

10. Mold as defined in claim 9, wherein said peripheral channel has an inner wall rising to the height of said basin rim and an outer wall rising substantially higher than said basin rim.

11. Mold as defined in claim 3, wherein said basin bottom has a substantially uniform thickness which is in the range extending from 0.05 mm to 1 mm.

12. Mold as defined in claim 3, wherein said basin walls have a height which is in the range extending from 5 to 15 mm.

* * * * *